United States Patent [19]

Draenert

[11] Patent Number: 4,713,076
[45] Date of Patent: Dec. 15, 1987

[54] COATING COMPOSITION AND ANCHORAGE COMPONENT FOR SURGICAL IMPLANTS

[76] Inventor: Klaus Draenert, Gabriel-Max-Strasse 3, Munich, Fed. Rep. of Germany

[21] Appl. No.: 724,103

[22] Filed: Apr. 17, 1985

[30] Foreign Application Priority Data

Apr. 19, 1984 [DE] Fed. Rep. of Germany ....... 3414924

[51] Int. Cl.$^4$ .............................. A61F 2/28; A61F 2/32
[52] U.S. Cl. .......................................... 623/16; 623/23; 128/924
[58] Field of Search ........................ 623/16, 17, 18, 19, 623/20, 21, 22, 23; 128/92 C, 92 CA, 92 G

[56] References Cited

U.S. PATENT DOCUMENTS

| 4,330,514 | 5/1982 | Nagai et al. ............................. 106/35 |
| 4,330,891 | 5/1982 | Branemark et al. ................. 128/92 G |
| 4,347,234 | 8/1982 | Wahlig et al. ............................ 623/16 |
| 4,355,428 | 10/1982 | Deloison et al. ....................... 3/1.91 |
| 4,373,217 | 2/1983 | Draenert ............................ 128/92 G |

FOREIGN PATENT DOCUMENTS

| 2620891 | 11/1977 | Fed. Rep. of Germany ........ 623/16 |
| 2917446 | 11/1980 | Fed. Rep. of Germany ........ 623/16 |
| 0058041 | 4/1983 | Japan ..................................... 623/16 |

Primary Examiner—Richard J. Apley
Assistant Examiner—David J. Isabella
Attorney, Agent, or Firm—Bucknam & Archer

[57] ABSTRACT

The invention relates to a coating composition and an anchorage component for implants having a completely or partly coated surface. The coating comprises a filling material of highly porous spherical particles having a diameter from about 10 to about 200 μm and a pore volume from about 25 to about 80% on the basis of solid calcium compounds and a resorbable binding agent (matrix).

15 Claims, 9 Drawing Figures

SECTION:

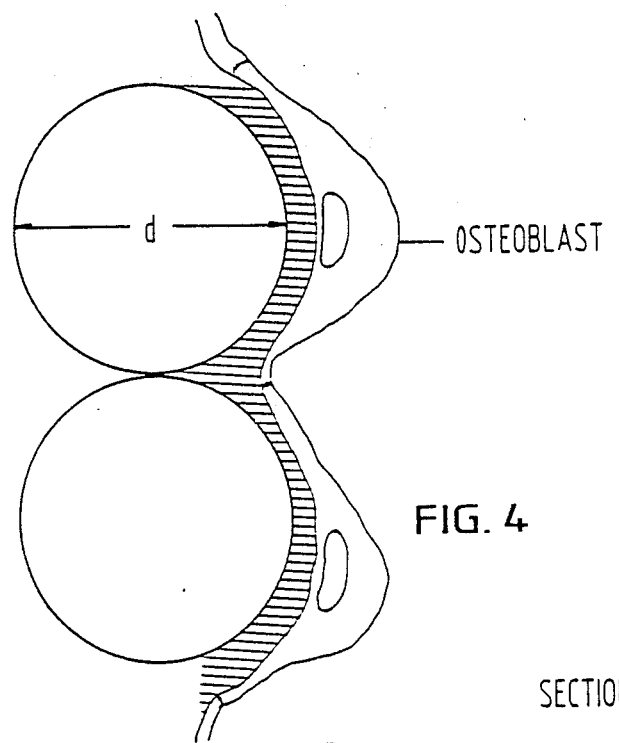
FIG. 4
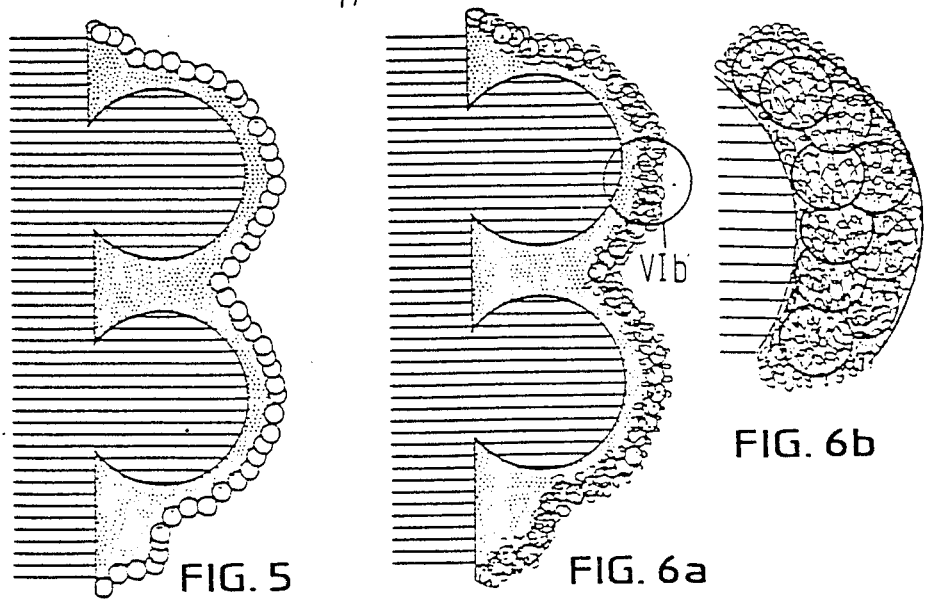
FIG. 5
FIG. 6a
FIG. 6b

DIAMETER:

TOP VIEW:

COATING COMPOSITION AND ANCHORAGE COMPONENT FOR SURGICAL IMPLANTS

FIELD OF THE INVENTION

The present invention relates to a coating composition for surgical implants comprising a resorbable binding agent and a filling material of highly porous spherical particles consisting of a solid calcium compound. The invention relates further to an anchorage component for surgical implants having a fully or partly coated surface, the coating comprising the mentioned coating composition. Due to its characteristic ultrastructure, the coated surface of the anchorage component allows in a special way the interlocking of the bone with the implant.

BACKGROUND OF THE INVENTION

A joint prosthetic component is usually anchored in the bone with a pin or a stem (anchorage component); see J. Bone Joint Surg., Vol. 21, pp. 269-288.

Various anchorage techniques are described in U.S. Pat. Nos. 2,934,065 and 2,718,288 and in French Pat. No. 1,278,359.

A hip joint is often replaced, e.g. by using a metal stem anchored in the medullary canal with bone cement; see J. Bone Joint Surg., Vol. 42 B, pp. 28-30.

The compatibility and the biomechanical strength of these bone cements is unsatisfactory, since the plastic materials serving as binding agents release parts to the surrounding tissue, which may cause harmful side reactions in the organism. In addition the reaction heat released during the hardening of the synthetic adhesive may damage the tissue. These and other reactions may cause a loosening of the prosthesis. Therefore attempts were made to provide cement-free anchorage systems, in order to have the prosthetic components anchored without the aid of the so-called bone cements see U.S. Pat. No. 3,605,123.

As a rule it is hereby necessary to enlarge the surface of the shaft of the prosthesis, e.g. by applying waved surfaces, saw teeth etc.; see e.g. German Pat. No. 837 294.

In the following attempts were made to modify the surface of the prosthetic shaft structurally in order to enlarge the surface and to thus allow bony ingrowth. Thus German Offenlegungsschrift No. 21 27 843 discloses a porous metal coating which is firmly bound to the basic body of the same material. With all these coatings it was found that bony ingrowth did occur only under specific conditions. However, reproducible results which would apply for all patients were not obtained with such prosthetic surfaces. It must be assumed that further factors are involved in securing bony ingrowth and prognostically accessible anchorage.

When examining the question in how far the individual osteoblast and/or the layer of osteoblasts may be induced by different morphological or chemical structures or substances to regenerate bones and/or to build up specific trabeculae, it was found that regarding the osteoblast a specific morphological sructure in the anchorage part strongly enhances bone regeneration, whereas with the layer of osteoblasts a different specific morphological structure caused the improved formation of supporting trabeculae. In addition, the specific embodiments (topography) of the prosthetic anchorage which are necessary in order to obtain optimal statical results must be taken into consideration in the overall construction. Moreover, the overall stress and the movement sequence of a joint in view of the design of the prosthesis which is decisive for the direction of force must also be taken into account.

From the criteria found here four dimensions of structuralization of implants resulted. In the following they are called structures of the first to the fourth order (structures I to IV). According to this definition the structure of the first order (structure I) corresponds to the external design of the prosthesis, i.e. the form of the anchorage part. The structure of the second order (structure II) represents a view of the surface (topography). With structure II, for example, specific surface designs, such as a waved surface or a saw teeth-like form of the prosthetic shaft, are designated. The surface designs of structure II are meant to enhance the mechanical anchorage. According to the present definition, the structure of the third order (structure III) represents the microstructure of the surfaces. It designates, for example, surface forms (e.g. small spherical particles) up to the mm-range. Finally, what is meant by the structure of the fourth order (structure IV) is the ultrastructure (up to a size of 30 um), which is essential for the present invention.

One embodiment of the above-mentioned structures I to III is described in German Pat. No. 27 30 004. This publication reveals the implant structure from the prosthesis' design (structure I) to the microstructure (structure III), which, for example, may be present in the form of a spherical coating. The projections on the surface of the basic body are meant to cause as improved interconnection of the osseous tissue in the interstices between the projections and thus a more resistant anchorage of the osseous tissue, preferably without a binder. The surface layer of this known implant, however, has the drawback, that it is not resorbable, and thus the osteocytes do not sufficiently adhere to the basic body. The biological and chemotactical activities (inducing of bone growth) are unsatisfactory with non-resorbable surfaces. Finally, no additions, such as hemostyptics, osteogenic substances, vaso-active substances and hormones acting on bone can be incorporated in the surface layer of German Pat. No. 27 30 004.

German Pat. No. 26 20 907 describes a coating of non-resorbable plastic material comprising spherical filing materials consisting of calcium phosphate, which is resorbable to a high degree. The non-resorbable plastic matrix has the disadvantage that the plastic material is abraded by the interfacial shearing action and that the wear particles are not resorbable, thus causing inflammations and possibly the loosening of the prosthesis.

A further considerable drawback of the coating according to German Pat. No. 26 20 907 consist in the fact that the ceramic particles stated to be resorbable suck themselves full with the non-resorbable plastic material, thereby leading to a further reduction in the resorbability of the coating. For this reason the osseous tissue around the prosthetic anchorage cannot grow deeply and rapidly onto the basic body (stem), this resulting in a loss of the stable fixation.

It is an object of the present invention to provide a fully resorbable coating composition for surgical implants.

It is a further object of the present invention to provide a fully resorbable coating composition for surgical implants which enables deep and rapid ingrowth of bone.

It is a further object of the present invention to provide an anchorage component for surgical implants with a fully or partly coated surface, wherein the coating is completely resorbable.

It is a further object of the present invention to provide an anchorage component for surgical implants with a fully or partly coated surface, the coating being completely resorbable and enabling deep and fast ingrowth of bone onto the basic body of the implant.

It is a further object of the present invention to provide an anchorage component for surgical implants with a fully or partly coated surface, said coating being completely resorbable, which anchorage component secures solid anchorage of the implant. It is still a further object of the present invention to provide a method for treating bone defects, which enables fast and deep ingrowth of the bone into the surface layer of the implant and which secures a firm anchorage of the implant.

The above and other objects and advantages of the present invention will be evident from the following description of the invention.

SUMMARY OF THE INVENTION

The present invention relates to a coating composition for surgical implants and to an anchorage component for surgical implants being coated on its surface with said coating composition. The coating composition is completely resorbable and enables fast and deep ingrowth of bone. The invention is based on the finding that there are essentially two factors which induce the desired bone ingrowth and may determine the morphology of a supporting or non-supporting bone structure, and the corresponding ability to resist stress acting on it. One factor is the morphology of the surface structure in the anchorage component and the other factor is the chemical composition of its surface.

It has been found that spherical particles or surface parts therefrom, the spherical particles having a diameter from about 10 to about 200 $\mu$m, preferably from about 15 to about 50 $\mu$m, constitute the optimally structured surface (ultrastructre IV), which an osteoblast can recognize as its basis.

A subject matter of the present invention is therefore a coating composition for surgical implants comprising a resorbable filling material on the basis of solid calcium compounds and a binding agent, characterized in that the binding agent is also resorbable and that the filling material comprises highly porous spherical particles having a diameter from about 10 to about 200 $\mu$m and a pore volume from about 25 to about 80%.

A further subject matter of the invention is an anchorage component of surgical implants having a fully or partly coated surface, the coating comprising a resorbable filling material on the basis of solid calcium compounds and a binding agent, characterized in that the binding agent is also resorbable and that the filling material comprises highly porous spherical particles having a diameter from about 10 to about 200 $\mu$m and a pore volume from about 25 to about 80%.

In a special embodiment the coating composition on the anchorage part may comprise additional armament. This armament may consist of fibers of specific length and thickness or of an interconnected network in the form of an prosthetic stocking.

Still another subject matter of the invention is a method for repairing a bony defect, charcterized by the use of an implant having an anchorage component as defined above.

BRIEF DESCRIPTION OF THE DRAWINGS

FIG. 4 shows schematically two spherical particles (filling material of the inventive coating composition), which form the basis of an osteoblast.

FIG. 5 shows a subject-matter similar to FIG. 2, the coating comprising, however, additional armament in the form of a chain of spherical particles.

FIG. 6a shows a subject-matter similar to FIG. 5, the armament, however being a multi-layered prosthetic stocking.

FIG. 6b shows a sectional enlargement of FIG. 6a.

FIG. 8 also shows the diameter and the top view of the spherical particle chain.

A special feature of the coating composition of the present invention which is used for the production of the inventive anchorage component consists in that it is completely resorbable (both matrix and filling material). A further characteristic feature may be seen in the above-mentioned surface structure IV (ultra-structure).

The filling material comprises highly porous spherical particles having a diameter from about 10 to 200 $\mu$m, preferably from about 15 to about 50 $\mu$m, the optimum being at about 20 $\mu$m. These spherical particles have a pore volume from about 25 to 80%, preferably from aoubt 50 to about 80%, and most preferably from about 50 to about 65%.

The ultrastructure according to the present invention induces the individual osteoblast or the layer of osteoblasts, respectively, to build up specific trabeculae. Moreover, the structure of the coating composition according to the present invention stimulates the individual osteocyte. Thus results a rather rapid ingrowth of the bone in the coating composition. In FIG. 4 represents d the diameter of the spherical particles which is preferably about 20 $\mu$m and has about the same size as the osteoblast.

The highly porous spherical particles constituting the filling material preferably comprise tricalcium phosphate or apatite (hydroxyl apatite). Their pores may be filled with a resorbable, biologically compatible material. This material is preferably the binding agent used. Examples for the resorbable, biologically compatible material or the binding agent, respectively, are polyamino acids, poly-lactates, polyglycolates, co-condensates of these substances, gelatine, collagen and calcium compounds. Preferably the filling materials are harder than the binding agent.

It was further found by the inventor that an organic matrix leads to a considerably faster formation of a layer of osteoblasts than a metal or ceramic surface. It was also found that, although the ceramic surface is better colonized than the metallic surface, the surface of the sintered apatite is even more rapidly colonized by cells than the ceramic surface. Furthermore it was found that a collagen matrix was even more rapidly colonized (populated) by cells than a purely ceramical or apatite surface. The best colonisation is obtained when the organic matrix (e.g. collagen) is armed with small spherical particles from apatite.

This coating composition is a preferred embodiment of structure IV (ultrastructure) according to the invention.

Figure 1:
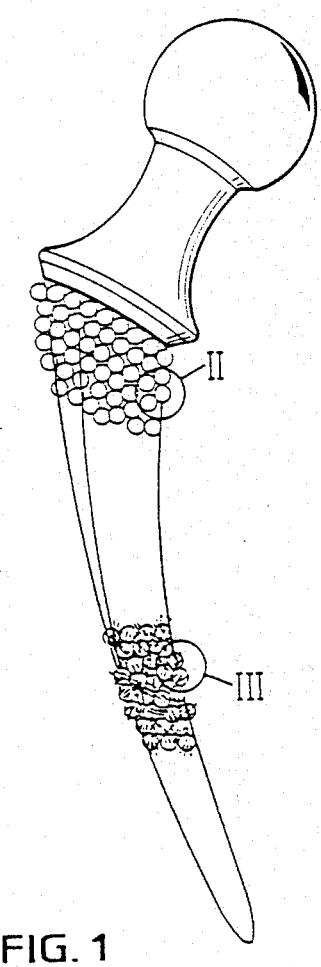
FIG. 1 shows the femoral component of a hip joint endoprosthesis with two embodiments of the inventive surface design of the anchorage component.
Figure 2:
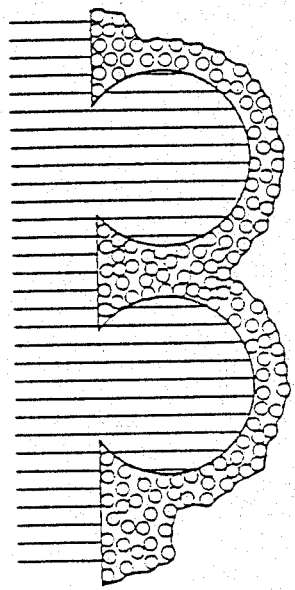
FIG. 2 presents a longitudinal section of an implant surface revealing two spherical elementary bodies (structure III) coated with a matrix comprising spherical filling particles.
Figure 3:
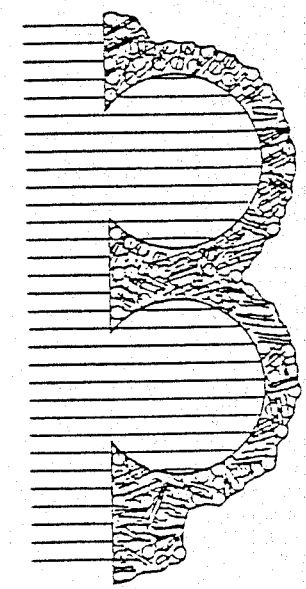
FIG. 3 shows a subject matter similar to FIG. 2, the coating, however, comprising additional armament in the form of fibers. These fibers have not been drawn at scale. In reality they are longer as can be derived from FIG. 1.
Figure 7:
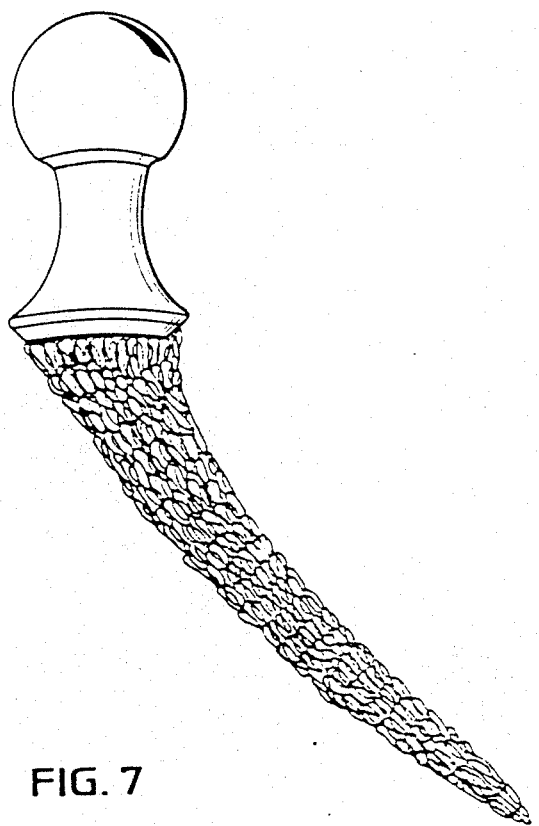
FIG. 7 shows an anchorage component of a prothesis as shown in FIG. 1 however with a stocking armament of the organic layer.
Figure 8A:
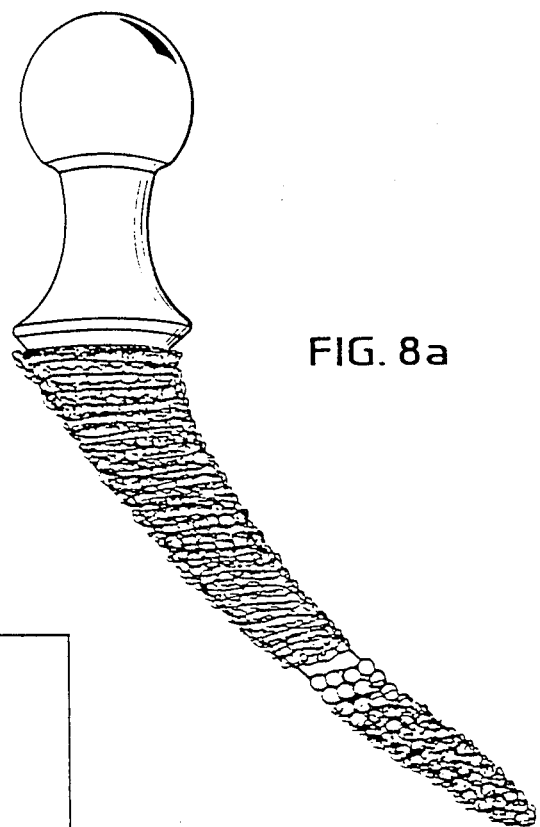
FIG. 8 shows an anchorage component of a prothesis as shown in FIG. 1 however with a stocking armament of the organic layer, the stocking having been applied to a coating consisting of a spherical particle chain stocking.
Figure 8B:
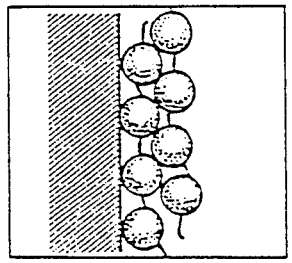
Figure 8C:
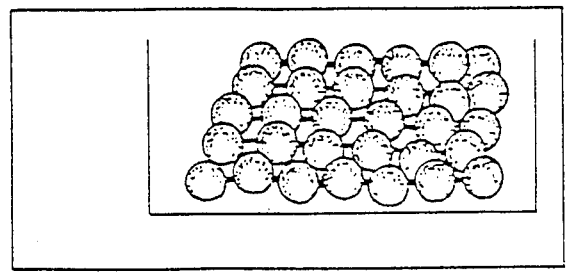

The coating composition of the invention is completely resorbable. A completely resorbable matrix has considerable advantages over a non-resorbable matrix. it is very rapidly resorbed in the zones of strain and replaced by osseous tissue. In relatively short period of time an interconnected layer of osteoblasts is obtained by a spherical arrangement of the structure III (see FIG. 2) in connection with a thin coating from the coating composition according to the invention which is applied to the spherical particles. This layer of osteoblasts is capable of forming a lamellar, stress withdrawing (resisting) bone.

The thickness of the spherical arrangement and its concrete size determine the specific structure of the arrangement of the osteoblasts. It is therefore not necessary to rearrange the cells and to remodel the formed trabeculae. Therefore no time for resorption and bone remodelling is necessary.

In one embodiment of the invention the layer of the coating composition on the anchorage component may comprise a further armament. this armament may comprise fibers of differing lengths, which have a thickness from about 100 to about 300 μm, in particular of about 200 μm. The fibers have preferably a length of more than about 2 to about 15 mm, more preferably at least about 3 mm and no more than about 10 mm, the optimal length being from about 4 to about 5 mm.

Examples for materials which may constitute the fiber-shaped filling materials are polyamino acids, polylactates, polyglycolates, co-condensates of these materials, gelatine, collagen, carbon or catgut. The amount of the fiber-shaped filling material for armament may be at about 5 to about 15%, preferably at about 10% based on the amount of the highly porous spherical particles.

In a further embodiment of the invention the additional armament is an interconnected network in form of a prosthetic stocking.

The prosthetic stocking may also comprise chains of spherical particles, wherein the spherical particles have a diameter from about 15 to about 50 μm, in particular about 20 μm, and wherein the spherical particles are packed so tightly that they touch each other in a three-dimensional arrangement. The chains of spherical particles may also be arranged in the form of a multi-layered stocking.

The preparation of the coating composition and of the anchorage component according to the invention are in following exemplified by the example of collagen as a completely resorbable binding agent. According to a usual method a collagen mass is prepared from animal bones. To this mass a spherical apatite or TCP may be added just like glue (in the present application the term "apatite" means preferably "hydroxyl apatite", "TCP" means tricalcium phosphate). By using infrasonic waves, shaking stirrers and/or other types of stirrers a tight spherical arrangement may be obtained. An implant is then impregnated with this coating composition. Thus the inventive structure IV forms a coating on structure III; see FIG. 2.

In the following an example is given for the preparation of a prosthetic stocking as additional armament. From the above-described collagen mass armed with apatite or TCP spherical particles of the optimal size from about 200 to about 3000 μm are prepared and stringed to chains of spherical particles on a resorbable thread. These spherical chains are processed in a circular knitting machine to continuous stockings, thus resulting in a network of spherical chains. From this network of spherical chains all kinds of multi-layered prosthetic stockings may be prepared by folding in each other. Spherical chain networks or prosthetic stockings may serve as additional armament of the anchorage parts; see FIGS. 5 and 6.

The coating composition of the invention may be applied to a prosthetic pin or stem. During drying the coating shrinks onto the anchorage component of the prosthetic and thus interconnects matrix, filling material and the basic material (stem). A thus coated prosthesis may be inserted into the bone without using bone cement as binding agent. In a short period of time continuous layers of osteoblasts develop on the treated surface and thus firmly support the prosthetic component in the bone. Distinctive supporting trabeculae are formed, beside which the matrix coating is resorbed so that in consequence the bone can grow deeply in the surface structure of the basic body (supporting structure of the stem). Through the inducing effect of the small spherical particles from apatite, which e.g. can be covered by collagen, growth regeneration and ingrowth of the implant into the bone is considerably faster than would be the case with usual coatings or un-coated implants.

The induction of osteogenesis can be further enhanced by the addition of chemically active agents in the matrix substance. For example, chemotactically acting materials from the bone matrix and necrotic bones are known, which comprise so-called bone morphogenic proteins, which have a special inducing effect on osteogenesis. The addition of such additives is preferred. It was found that the induction of osteogenesis is particularly favourable if the highly porous spherical particles used as filling material are harder than the surrounding matrix, so that they exert a mechanically stimulating effect on the osteoblasts. Such an embodiment is also preferred.

A further advantage of the inventive anchorage component consists in the fact that is comprises a considerable amount of a binding agent. It was found that the binding agent has a remarkable capacity for release regarding the addition of active agents. It is known that implants which are not accessible to body defense due to the deficiency in vascularization, are endangered by the fact that they are easily populated by bacteria. This can be prevented by adding an antibiotic to the coating composition. Such admixtures of antibiotics are well-known from bone cements, where they have been extensively tested. This kind of protection has so far not been available for cement-free prosthetic devices. However, with the coating composition of resorbable materials it is possible to provide the cement-free prosthetic devices and implants, regardless of the kind, prophylactically with an effective protection against infections.

The local application of other medicaments, such as hemostyptics, is known from external treatments. By adding such substances to the coating composition of the invention such active agents can become effective even where the organs are not accessible to external treatment. Hemostyptics as components of the binding agent cause the immediate hemostasis in the osseous bed. Vasoactive substances, such as noradrenaline or one of its derivatives, have also a hemostatic effect by means of vasoconstriction. Thus it is prevented that the boundary layer is soaked with blood and so the mechanical strength of the boundary zone is sustained for a longer period of time. Further, as already mentioned, bone-inducing, chemotactically active substances may be admixed to the binding agent. They speed up bone formation. Substances such as calcitonine render hormone applications locally effective and thus prevent the decomposition of the newly formed bone.

The invention is illustrated by the example.

EXAMPLE

Preparation of an Anchorage Component Having a Completely Resorbable Coating

In the following example the coating of the anchorage component for implants comprises highly porous tricalcium phosphate in the form of spherical particles as filling material. The anchorage component is additionally armed with a resorbable prosthetic stocking.

1.1. First a fabric (e.g. a continuous stocking) is knitted on a usual circular knitting machine (Dubier, Neuchatel, France) with a resorbable thread having a thickness of 200 μm. This stocking is placed on the prosthesis in such a way that it can be pulled over the anchorage component by twisting for 90° to 180°, thus forming a second layer. By twisting the stocking again over the head of the prosthesis a third layer is applied. Thus a multi-layered stocking can be pulled over the stem of the prosthesis. The fabric can be kept on the stem of the prosthesis under any prior tension. Subsequently the stem of the prosthesis which has been covered with the stockings is coated with a sticky mass comprising spherical particles of tricalciu phosphate (diameter 15 to 50 μm). The coating is applied by laying on or by immersing the prosthesis. Then the mass is dried and hardens. It forms a continuous coat with a fine and a coarse surface structure around the anchorage component of the prosthesis or around an implant.

1.2. The resorbable matrix may be prepared in a very simple and econimical way by obtaining collagen from animal bones and by processing it analoguously to the known methods for preparing bone glue to a plastic and sticky material. The chemical processes on which this method is based are known. They consist essentially in the precipitation of the protein, the swelling of the collagen and their demineralization. The collagen substances obtained from these known processes have no longer any antigenic properties and are thus biologically inert.

The collagen mass thus prepared from animal bones is subsequently dried and further processed to granules. The granules can be further processed to a dough-like mass by adding a physiological solution of electrolytes and further by adding highly porous spherical particles of tricalcium phosphate in the size claimed. The dough-like mass is adjusted to the desired viscosity by adding alcohol and a solution of electrolytes.

1.3. The coating of the implant may for example be applied by immersion. If the used collagen mass has low and medium viscosity the implant is immersed. The sticky mass thereby adheres to the anchorage part of the prosthesis and covers it with a continuous coat. By shrinkage of the matrix during the drying process a reprint-like adjustment to the anchorage part is obtained.

A further coating method is the fine spraying of the matrix coat or a coating by means of electrostatic charge, whereby a continuous and extremely thin coat is applied to the prosthesis. The respective methods are known from finishing processes in the automobile industry.

However, the coating may also be applied by the pressing-on of the matrix under high pressure.

Finally, the coating may be applied via a melting process, in particular if polyamino acids or polyglycolates are used.

1.4. When preparing the inventive highly porous tricalcium phosphates in the form of spherical particles the following chemical reactions occur:

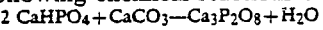
$$2\ CaHPO_4 + CaCO_3 \rightarrow Ca_3P_2O_8 + H_2O$$

Tricalcium phosphate is essentially obtained from a powder mixture of calcium hydrogen phosphate and calcium carbonate in a ration of 2:1. From it a tricalcium phosphate in the α- or β-form is obtained by sintering and pressing at temperatures around 1500° C. By rapid cooling a highly porous tricalcium phosphate in sintered form can be prepared. It has a porosity from 25 to 80% as required in the invention.

This form of the tricalcium phosphate is particularly rapidly resorbable. From this material the corresponding spherical particles can be prepared in the ball mill. The desired size fractions are obtained by sieving in a manner known per se.

1.5. Spherical particles of tricalcium phosphate can also be prepared from powder. In this case a mixture of the resorbable matrix (e.g. a collagen matrix) is prepared from powdered tricalcium phosphate. For example, 5 g collagen and 2 g tricalcium phosphate as fine, commercially available powder are mixed. By drying this mass a solid substance is obtained which again can be processed into a tricalcium phosphate matrix consisting of fine spherical particles by crushing, subjecting to treatment in the ball mill, and sieving.

What is claimed is:

1. A resorbable coating composition for anchorage components for surgical implants, consisting of a dried resorbable filling material and a resorbable binding agent, wherein the filling material consists of porous spherical particles containing solid tricalcium phosphate or apatite and having a diameter from about 15 to 50 μm and a pore volume from about 25 to about 80%, the pores of the spherical particles being filled with the resorbable binding agent.

2. A coating composition according to claim 1, wherein the binding agent is a member selected from the group consisting of a polyamino acid, a polylactate, a polyglycolate, a co-condensate thereof, gelatin, collagen and calcium compound.

3. The coating composition according to claim 1, wherein the spherical particles are harder than the binding agent.

4. The coating composition according to claim 1, wherein the spherical particles have a diameter of about 20 μm.

5. The coating composition according to claim 1, wherein the pore volume of said spherical particles is 50-65%.

6. A coating composition for anchorage components for surgical implants, consisting of a dried resorbable filling material and a resorbable binding agent, wherein the filling material consists of porous spherical particles containing solid tricalcium phosphate or apatite and having a diameter from about 15 to 50 μm and a pore volume from about 25 to 80%, the pores of the spherical particles being filled with the binding agent and at least one additive which is a member selected from the group consisting of hemostypics, osteogenic substances, antibiotics, vaso-active substances and hormones acting on bone.

7. Anchorage component for surgical implants having a fully or partly coated surface with a coating composition according to claim 1.

8. An anchorage component for surgical implants having a fully or partly coated surface, with a coating composition consisting of a dried resorbable filling material and a resorbable binding agent, wherein the filling material consists of porous spherical particles containing solid tricalcium phosphate or apatite and having a diameter from about 15 to 50 μm and a pore volume from about 25 to about 80%, the pores of the spherical particles being filled with the binding agent and additional reinforcing material.

9. The anchorage component according to claim 8, wherein the reinforcing material consists of fibers of length of 2 to 15 mm and a thickness from about 100 to about 300 μm.

10. The anchorage component according to claim 8, wherein the fibers are a member selected from the group consisting of polyamino acid, a polylactate, a polyglycolate, a co-condensate thereof, gelatin, collagen, carbon and catgut.

11. The anchorage component according to claim 8, wherein the reinforcing material forms a stocking shaped network.

12. The anchorage component according to claim 11, wherein said network is made of a chain of spherical particles having a diameter from about 15 to aboug 50 μm, and wherein the spherical particles are packed so tightly that they touch each other in a three-dimensional arrangement.

13. The anchorage component according to claim 11, wherein said stocking shaped network is a multilayer stocking.

14. A method of filling in a defect in a bone which consists of anchoring in the bone a surgical implant having an anchorage component which has a fully or partly coated surface, with a coating composition which consists of a dried resorbable filling material and a resorbable binding agent, wherein the filling material consists of porous spherical particles containing solid tricalcium phosphate or apatite and having a diameter from about 15 to 50 μm and a pore volume from about 25 to about 80%, the pores of the spherical particles being filled with the binding agent.

15. The method according to claim 14, wherein osteoblasts are formed during the bone regeneration process and the osteoblasts are formed on the spherical particles.

* * * * *